United States Patent
Kirilin et al.

(10) Patent No.: US 12,227,465 B2
(45) Date of Patent: Feb. 18, 2025

(54) METHODS FOR PRODUCING $C_2$ TO $C_5$ PARAFFINS USING A HYBRID CATALYST COMPRISING A HIGH ACIDITY MICROPOROUS COMPONENT

(71) Applicant: Dow Global Technologies LLC, Midland, MI (US)

(72) Inventors: Alexey Kirilin, Terneuzen (NL); Adam Chojecki, Ghent (BE); Joseph F. Dewilde, Midland, MI (US); Glenn Pollefeyt, Wondelgem (BE); Davy L.S. Nieskens, Terneuzen (NL); Andrzej Malek, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 587 days.

(21) Appl. No.: 17/613,241

(22) PCT Filed: May 7, 2020

(86) PCT No.: PCT/US2020/031819
§ 371 (c)(1),
(2) Date: Nov. 22, 2021

(87) PCT Pub. No.: WO2020/236431
PCT Pub. Date: Nov. 26, 2020

(65) Prior Publication Data
US 2022/0220044 A1  Jul. 14, 2022

Related U.S. Application Data

(60) Provisional application No. 62/851,999, filed on May 23, 2019.

(51) Int. Cl.
C07C 1/04 (2006.01)
B01J 21/06 (2006.01)
(Continued)

(52) U.S. Cl.
CPC .............. C07C 1/043 (2013.01); B01J 21/063 (2013.01); B01J 21/066 (2013.01); B01J 23/06 (2013.01);
(Continued)

(58) Field of Classification Search
CPC . C07C 1/043; C07C 2521/06; C07C 2523/06; C07C 2523/08; C07C 2523/10;
(Continued)

(56) References Cited

U.S. PATENT DOCUMENTS

| 4,440,871 A | 4/1984 | Lok et al. |
| 6,376,562 B1 | 4/2002 | Ihm et al. |

FOREIGN PATENT DOCUMENTS

| CN | 109261199 A | 1/2019 |
| WO | 2016/0007607 A1 | 1/2016 |
| WO | 2019/089206 A1 | 5/2019 |

OTHER PUBLICATIONS

Liu, X. et al., "Design of efficient bifunctional catalysts for direct conversion of syngas into lower olefins: Via methanol/dimethyl ether intermediates", Chemical Science, vol. 9, No. 20, pp. 4708-4718 (May 28, 2018).
(Continued)

Primary Examiner — Jafar F Parsa
(74) Attorney, Agent, or Firm — Dinsmore & Shohl LLP

(57) ABSTRACT

A method for preparing $C_2$ to $C_5$ paraffins including introducing a feed stream of hydrogen gas and a carbon-containing gas selected from carbon monoxide, carbon dioxide, and mixtures thereof into a reaction zone of a reactor. Converting the feed stream into a product stream that includes $C_2$ to $C_5$ paraffins in the reaction zone in the presence of a hybrid catalyst. The hybrid catalyst including a microporous catalyst component; and a metal oxide catalyst component. The metal oxide catalyst component including a metal component present on a metal oxide support material. The metal oxide support material includes at least one oxide of a metal selected from Group 4 of the IUPAC periodic table of elements. The product stream has a $C_3/C_2$ carbon molar ratio greater than or equal to 4.0.

13 Claims, 1 Drawing Sheet

(51) Int. Cl.

| | | |
|---|---|---|
| *B01J 23/06* | (2006.01) | |
| *B01J 23/08* | (2006.01) | |
| *B01J 23/10* | (2006.01) | |
| *B01J 29/85* | (2006.01) | |
| *B01J 35/61* | (2024.01) | |
| *B01J 35/63* | (2024.01) | |
| *B01J 37/02* | (2006.01) | |
| *B01J 37/04* | (2006.01) | |
| *B01J 37/08* | (2006.01) | |

(52) U.S. Cl.
CPC .............. *B01J 23/08* (2013.01); *B01J 23/10* (2013.01); *B01J 29/85* (2013.01); *B01J 35/613* (2024.01); *B01J 35/615* (2024.01); *B01J 35/633* (2024.01); *B01J 35/635* (2024.01); *B01J 37/0201* (2013.01); *B01J 37/0236* (2013.01); *B01J 37/04* (2013.01); *B01J 37/088* (2013.01); *C07C 2521/06* (2013.01); *C07C 2523/06* (2013.01); *C07C 2523/08* (2013.01); *C07C 2523/10* (2013.01); *C07C 2529/85* (2013.01)

(58) Field of Classification Search
CPC .............. C07C 2529/85; B01J 2523/00; B01J 29/7015; C10G 2/00
See application file for complete search history.

(56) References Cited

OTHER PUBLICATIONS

International Search Report and Written Opinion issued by the European Patent Office acting as International Searching Authority for International Patent Application No. PCT/US2020/031819 dated Aug. 12, 2020 (16 total pages).
International Preliminary Report on Patentability for Application No. PCT/US2020/031819, issued Nov. 16, 2021, pp. 1-8.
Communication pursuant to Rules 161 (1) and 162 for EP Application No. 20728857.2, issued on Jan. 10, 2022, pp. 1-3.
Jiao, Selective conversion of syngas to light olefins, Science Mag. org, Mar. 4, 2016, 1-4, vol. 351, Issue 6277.
Cheng, Direct and Highly Selective Conversion of Synthesis Gas to Lower Olefins: Design of a Bifunctional Catalyst Combining Methanol Synthesis and Carbon-Carbon Coupling, Angewandte Chemie, 2016, 1-5, vol. 55.
Deimund, Effect of Heteroatom Concentration in SSZ-13 on the Methanol-to-Olefins Reaction, American Chemical Society, 2016, 542-550, vol. 6.
Bleken, The Effect of Acid Strength on the Conversion of Methanol to Olefins Over Acidic Microporous Catalysts with the CHA Topology, Top Catal, Jan. 7, 2009, 218-228, Springer Science Business Media LLC.
Bleken, The effect of acid strength on the MTO reaction, Thesis for the Masters Degree in Chemistry, University of Osloensis, Department of Chemistry, Dec. 2007, 1-149.
Argentina Office Action dated Dec. 26, 2023, pertaining to AR Patent Application No. 2020 01 01306, 3 pgs.
Chinese Office Action dated Jan. 3, 2024, pertaining to CN Patent Application No. 202080044259.X, 6 pgs.
Brazilian Technical Report dated Jun. 5, 2024, pertaining to BR 11 2021 023463.2, 8 pgs.

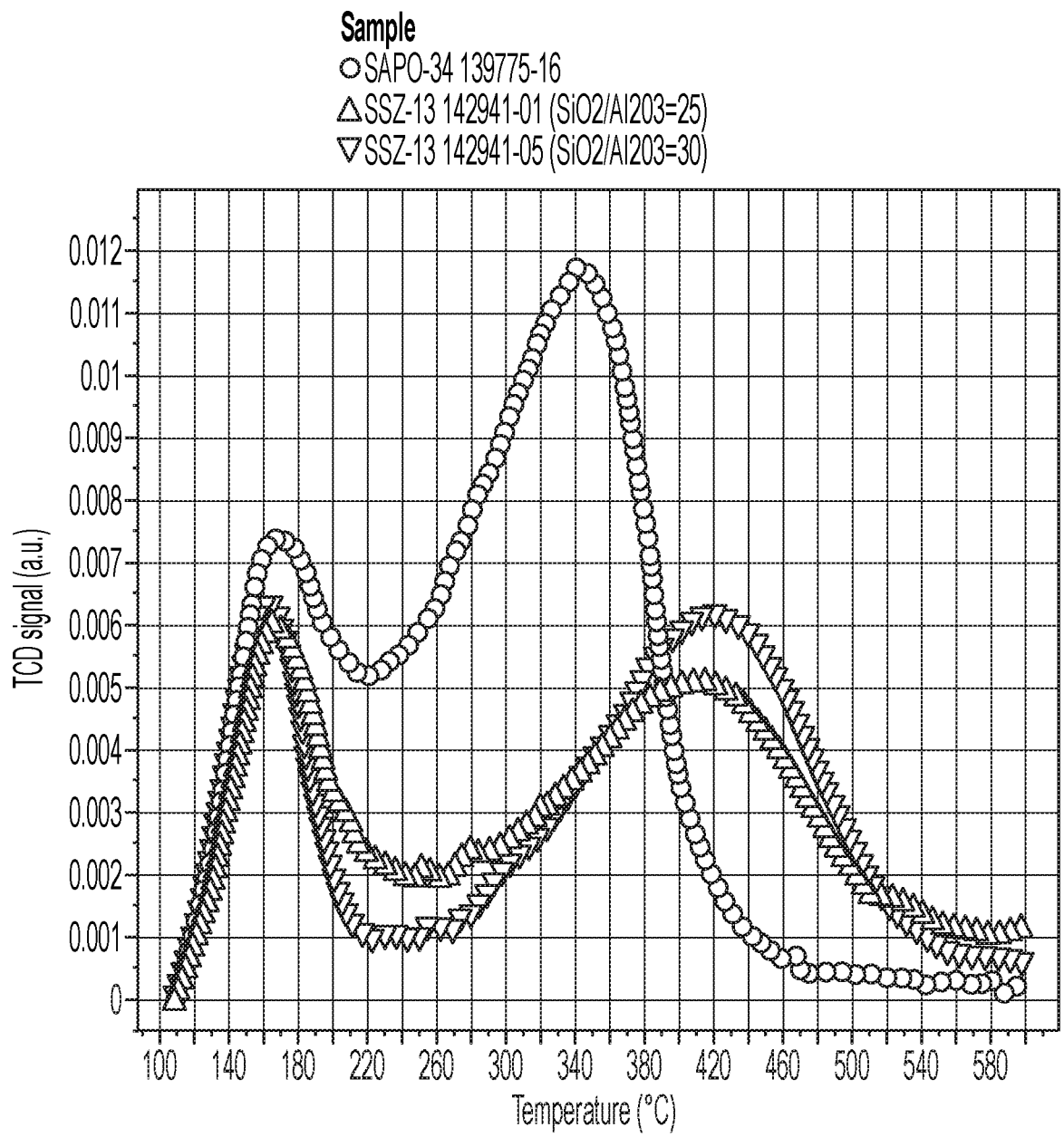

US 12,227,465 B2

METHODS FOR PRODUCING $C_2$ TO $C_5$ PARAFFINS USING A HYBRID CATALYST COMPRISING A HIGH ACIDITY MICROPOROUS COMPONENT

CROSS REFERENCE TO RELATED APPLICATIONS

This application claims priority to U.S. Provisional Patent Application No. 62/851,999, filed on May 23, 2019, the entire disclosure of which is hereby incorporated by reference.

BACKGROUND

Field

The present specification generally relates to catalysts that comprise a high acidity microporous catalyst component and methods that efficiently convert various carbon-containing streams to $C_2$ to $C_5$ paraffins. In particular, the present specification relates to hybrid catalysts comprising a high acidity microporous catalyst component and methods to achieve a high conversion of synthesis gas feeds and high yield of desired products, such as, for example, propane. The synthesis gas comprises hydrogen gas and a carbon-containing gas selected from the group consisting of carbon monoxide, carbon dioxide, and mixtures thereof. A hybrid catalyst generally comprises a combination of a metal oxide component and a microporous catalyst component that operate in tandem.

Technical Background

For a number of industrial applications, a desirable starting material is a lower hydrocarbon, including in particular $C_2$ to $C_5$ paraffins that can then be converted to olefins, for use in or as starting materials to produce plastics, fuels, and various downstream chemicals. These $C_2$ to $C_5$ materials may be saturated or unsaturated and therefore may include ethane, ethylene, propane, propylene, butanes, butylenes, pentanes, or pentenes. A variety of processes for producing these lower hydrocarbons has been developed, including petroleum cracking and various synthetic processes.

Synthetic processes for converting feed carbon to desired products, such as paraffins, are known. Some of these synthetic processes begin with the use of a hybrid catalyst. Different types of catalysts have also been explored, as well as different kinds of feed streams and proportions of feed stream components. However, many of these synthetic processes have low carbon conversion and much of the feed carbon either (1) does not get converted and exits the process in the same form as the feed carbon; (2) is converted to $CO_2$; or (3) carbon is converted to less desirable hydrocarbons. For example, many synthetic processes tend to favor methane or ethane production over propane production.

Accordingly, a need exists for hybrid catalysts and methods that have a high conversion of feed carbon to desired products with high selectivity, such as, for example, $C_2$ to $C_5$ paraffins—and particularly propane—in combination with reduced operating temperatures.

BRIEF DESCRIPTION OF THE DRAWING

FIG. 1 graphically depicts an Ammonia TPD plot for SAPO-34 and SSZ-13.

SUMMARY

According to one embodiment, a method for preparing $C_2$ to $C_5$ paraffins comprises: introducing a feed stream comprising hydrogen gas and a carbon-containing gas selected from the group consisting of carbon monoxide, carbon dioxide, and mixtures thereof into a reaction zone of a reactor; and converting the feed stream into a product stream comprising $C_2$ to $C_5$ paraffins in the reaction zone in the presence of a hybrid catalyst, the hybrid catalyst comprising: a microporous catalyst component; and a metal oxide catalyst component comprising a metal component present on a metal oxide support material, wherein the metal oxide support material comprises at least one oxide of a metal selected from Group 4 of the IUPAC periodic table of elements, wherein the product stream has a $C_3/C_2$ molar ratio greater than or equal to 4.0.

According to embodiments, the microporous catalyst component is silico-aluminate with Chabazite structure (CHA) and the Brönsted acid site concentration of the microporous catalyst component is greater than or equal to 0.25 mmol/g.

According to embodiments, a hybrid catalyst comprises: a metal oxide catalyst component comprising a metal component present on a metal oxide support material, wherein the metal oxide support material comprises at least one oxide of a metal selected from Group 4 of the IUPAC periodic table of elements; and a microporous catalyst component having a Brönsted acid site concentration greater than or equal to 0.35 mmol/g, and a Brönsted acid site strength from 380° C. to 500° C. measured as $NH_3$—desorption at rate of 5° C./min.

Additional features and advantages will be set forth in the detailed description that follows, and in part will be readily apparent to those skilled in the art from that description or recognized by practicing the embodiments described herein, including the detailed description which follows and the claims.

It is to be understood that both the foregoing general description and the following detailed description describe various embodiments and are intended to provide an overview or framework for understanding the nature and character of the claimed subject matter.

DETAILED DESCRIPTION

Reference will now be made in detail to embodiments of hybrid catalysts and methods using the hybrid catalyst to prepare $C_2$ to $C_5$ paraffins. In one embodiment, a method for preparing $C_2$ to $C_5$ paraffins comprises: introducing a feed stream comprising hydrogen gas and a carbon-containing gas selected from the group consisting of carbon monoxide, carbon dioxide, and mixtures thereof into a reaction zone of a reactor; and converting the feed stream into a product stream comprising $C_2$ to $C_5$ paraffins in the reaction zone in the presence of a hybrid catalyst, the hybrid catalyst comprising: a microporous catalyst component; and a metal oxide catalyst component comprising a metal component present on a metal oxide support material, wherein the metal oxide support material comprises at least one oxide of a metal selected from Group 4 of the IUPAC periodic table of elements, wherein the product stream has a $C_3/C_2$ molar ratio greater than or equal to 4.0.

The use of hybrid catalysts to convert feed streams comprising carbon to desired products, such as, for example, $C_2$ to $C_5$ paraffins, is known. However, many known hybrid catalysts require high temperatures to convert carbon-containing streams to $C_2$ to $C_5$ paraffins. For instance, hybrid catalysts comprising SAPO-34 microporous catalyst components operate at temperatures of 400° C. or greater to convert a carbon-containing stream, such as, for example, syngas, to $C_2$ to $C_5$ paraffins. Additionally, hybrid catalysts comprising a copper-containing mixed metal oxide typically render a hydrocarbon product distribution ranging from $C_2$ to $C_5$ paraffins, with high ethane selectivity. In contrast, hybrid catalysts disclosed and described herein exhibit a good yield of $C_2$ to $C_5$ paraffins—and particularly propane—even at temperatures of 380° C. or below. The composition of such hybrid catalysts used in embodiments is discussed below.

As a summary, hybrid catalysts closely couple sequential reactions on each of the two independent catalysts. In the first step, a feed stream comprising hydrogen gas ($H_2$) and at least one of carbon monoxide (CO), carbon dioxide ($CO_2$), or a mixture of CO and $CO_2$, such as, for example, syngas, is converted into oxygenated hydrocarbons. In the second step, these oxygenates are converted into hydrocarbons (mostly short chain hydrocarbons, such as, for example $C_2$ to $C_5$ paraffins). The continued withdrawal of oxygenates formed in the first step by the reactions of the second step ensures that there is no thermodynamic limit on the first reaction step to achieve the overall close to 100% (>99.9%) feed carbon conversion to hydrocarbons.

Hybrid catalyst systems comprise a metal oxide catalyst component, which converts the feed stream to oxygenated hydrocarbons, and a microporous catalyst component (such as, for example, a zeolite component), which converts the intermediate oxygenated products to hydrocarbons. In particular, SAPO-34 microporous catalyst components have been used in hybrid catalysts to convert carbon oxides to $C_2$-$C_4$ hydrocarbons. Typically, the process required to use a SAPO-34 microporous catalyst component to efficiently convert carbon oxides in carbon-containing streams to $C_2$-$C_4$ hydrocarbons requires demanding temperature conditions, such as 400° C. or greater to achieve a high conversion and avoid the presence of unconverted oxygenated products in the product stream.

However, embodiments disclosed and described herein use a metal oxide catalyst component and SSZ-13 zeolite as the microporous catalyst component. This combination of a metal oxide catalyst component and SSZ-13 produces $C_2$-$C_5$ paraffins at relatively low process temperatures, such as 380° C. or less, with a high selectivity to $C_3$ paraffin (propane). Although SSZ-13 and SAPO-34 are isostructural (i.e., both have small-pore 8MR pore openings and CHA crystal structure), only the use of SSZ-13 zeolite as the microporous catalyst component combined with a selected mixed metal oxide component in a hybrid catalyst leads to an increased formation of propane (also referred to as the "$C_3$ fraction") in comparison to a typical product distribution observed over SAPO-34 containing hybrid mixtures. Embodiments disclosed and described herein also provide a hybrid catalyst comprising a metal oxide component and microporous catalyst component that can be tuned to provide high output of a targeted $C_2$ to $C_5$ paraffin, such as propane.

Metal Oxide Catalyst Component

Hybrid catalysts disclosed herein comprise a metal oxide catalyst component. It should be understood that, as used herein, the "metal oxide catalyst component" includes metals in various oxidation states. In some embodiments, the metal oxide catalyst component may comprise more than one metal oxide and individual metals within the metal oxide catalyst component may have different oxidation states.

According to embodiments, the metal oxide catalyst component comprise a member selected from the group consisting of zinc (Zn), indium (In), gallium (Ga), lanthanum (La), aluminum (Al), chromium (Cr), and mixtures thereof. In embodiments, the metal oxide catalyst component is a supported metal oxide catalyst component. As used herein, a "supported metal oxide catalyst component" refers to a metal oxide catalyst component where some elements that make up the metal oxide catalyst component are supported by other elements or compounds.

In embodiments, the metal oxide catalyst component is a supported metal oxide catalyst component where elements, such as, for example, the elements previously described, are added to a support structure to form the supported metal oxide catalyst component. Subsequently, the supported metal oxide catalyst component is added to the microporous catalyst component. In some embodiments, the support comprises an oxide of a metal selected from Group 4 of the International Union of Pure and Applied Chemistry (IUPAC) periodic table of elements. According to embodiments, the support comprises, consists essentially of, or consists of titania ($TiO_2$), or comprises, consists essentially of, or consists of zirconia ($ZrO_2$). It should be understood that the supports used herein may be any polymorph of titania or zirconia. In some embodiments, the support may be, for example, anatase $TiO_2$, rutile $TiO_2$, brookite $TiO_2$, and mixtures thereof. In some embodiments, the support may be, for example, monoclinic $ZrO_2$, tetragonal $ZrO_2$, cubic $ZrO_2$, and mixtures thereof. According to some embodiments, the support may have a BET surface area that is greater than or equal to 40 meters squared per gram ($m^2$/g), such as greater than 50 $m^2$/g, greater than 60 $m^2$/g, greater than 70 $m^2$/g, greater than 80 $m^2$/g, greater than 90 $m^2$/g, greater than 100 $m^2$/g, greater than 110 $m^2$/g, greater than 120 $m^2$/g, greater than 130 $m^2$/g, greater than 140 $m^2$/g, greater than 150 $m^2$/g, greater than 160 $m^2$/g, greater than 170 $m^2$/g, greater than 180 $m^2$/g, or greater than 190 $m^2$/g. According to some embodiments, the maximum BET surface area of the support is 400 $m^2$/g. It should be understood that this maximum BET surface area may be applied as a maximum to any of the above ranges according to embodiments disclosed herein. Accordingly, in some embodiments, the BET surface area of the $TiO_2$ support is from 40 $m^2$/g to 400 $m^2$/g, such as from 50 $m^2$/g to 400 $m^2$/g, from 60 $m^2$/g to 400 $m^2$/g, from 70 $m^2$/g to 400 $m^2$/g, from 80 $m^2$/g to 400 $m^2$/g, from 90 $m^2$/g to 400 $m^2$/g, from 100 $m^2$/g to 400 $m^2$/g, from 110 $m^2$/g to 400 $m^2$/g, from 120 $m^2$/g to 400 $m^2$/g, from 130 $m^2$/g to 400 $m^2$/g, from 140 $m^2$/g to 400 $m^2$/g, from 150 $m^2$/g to 400 $m^2$/g, from 170 $m^2$/g to 400 $m^2$/g, from 180 $m^2$/g to 400 $m^2$/g, or from 190 $m^2$/g to 400 $m^2$/g. In some embodiments, the BET surface area of the support is from 80 $m^2$/g to 180 $m^2$/g, such as from 90 $m^2$/g to 170 $m^2$/g, from 100 $m^2$/g to 160 $m^2$/g, from 110 $m^2$/g to 150 $m^2$/g, from 120 $m^2$/g to 140 $m^2$/g, or about 130 $m^2$/g.

On or more elements, such as Zn, In, Ga, Cr, La, and mixtures thereof, may be added to the support by any suitable method. However, in some embodiments, the one or more elements are added to the support by any conventional method, such as, for example, impregnation, incipient wetness impregnation, etc. In embodiments, elements may be added to the support via an aqueous solution of a precursor material—such as nitrates of the above elements—added to the support particles in a dosed amount (such as dropwise) while vigorously shaking providing mixing sufficient to uniformly impregnate the support particles the support particles. It should be understood that the total amount of the precursor material that is mixed with the support particles will be determined on the desired target amount of the elements in the metal oxide catalyst component. Once the precursor and support particles are adequately mixed, the resulting metal oxide catalyst component may be dried at temperatures less than 200° C., such as less than 175° C., or less than 150° C. According to some embodiments, and subsequent to the drying, the metal oxide catalyst component may be calcined at temperatures from 300° C. to 800° C., such as from 425° C. to 775° C., from 450° C. to 750° C., from 475° C. to 725° C., from 500° C. to 700° C., from 525° C. to 675° C., from 550° C. to 650° C., from 575° C. to 625° C., or about 600° C.

The concentration of the one or more elements in the metal oxide component may be defined as a weight percentage based upon the total weight of the metal oxide catalyst component. For example, where the metal oxide catalyst component comprises zinc supported on a $TiO_2$ support, the weight percent of zinc is expressed as a percentage of zinc to the total amount of zinc and titanium oxides in the metal oxide catalyst component. Accordingly, in some embodiments, the weight percent of the one or more elements in the metal oxide catalyst component may be from 0.1 wt % to 10.0 wt %, such as from 0.5 wt % to 10.0 wt %, from 1.0 wt % to 10.0 wt %, from 1.5 wt % to 10.0 wt %, from 2.0 wt % to 10.0 wt %, from 2.5 wt % to 10.0 wt %, from 3.0 wt % to 10.0 wt %, from 3.5 wt % to 10.0 wt %, from 4.0 wt % to 10.0 wt %, from 4.5 wt % to 10.0 wt %, from 5.0 wt % to 10.0 wt %, from 5.5 wt % to 10.0 wt %, from 6.0 wt % to 10.0 wt %, from 6.5 wt % to 10.0 wt %, from 7.0 wt % to 10.0 wt %, from 7.5 wt % to 10.0 wt %, from 8.0 wt % to 10.0 wt %, from 8.5 wt % to 10.0 wt %, from 9.0 wt % to 10.0 wt %, or from 9.5 wt % to 10.0 wt %. In some embodiments, the weight percent of the one or more elements in the metal oxide catalyst component is from 0.1 wt % to 9.5 wt %, such as from 0.1 wt % to 9.0 wt %, from 0.1 wt % to 8.5 wt %, from 0.1 wt % to 8.0 wt %, from 0.1 wt % to 7.5 wt %, from 0.1 wt % to 7.0 wt %, from 0.1 wt % to 6.5 wt %, from 0.1 wt % to 6.0 wt %, from 0.1 wt % to 5.5 wt %, from 0.1 wt % to 5.0 wt %, from 0.1 wt % to 4.5 wt %, from 0.1 wt % to 4.0 wt %, from 0.1 wt % to 3.5 wt %, from 0.1 wt % to 3.0 wt %, from 0.1 wt % to 2.5 wt %, from 0.1 wt % to 2.0 wt %, from 0.1 wt % to 1.5 wt %, from 0.1 wt % to 1.0 wt %, or from 0.1 wt % to 0.5 wt %. In some embodiments, the weight of the one or more elements in the metal oxide catalyst component is from 0.5 wt % to 9.5 wt %, such as from 1.0 wt % to 9.0 wt %, from 1.5 wt % to 8.5 wt %, from 2.0 wt % to 8.0 wt %, from 2.5 wt % to 7.5 wt %, from 3.0 wt % to 7.0 wt %, from 3.5 wt % to 6.5 wt %, from 4.0 wt % to 6.0 wt %, or from 4.5 wt % to 5.5 wt %.

In embodiments, the metal oxide catalyst component comprises one or more of Zn, In, Ga, Cr and La supported on titania or zirconia. In some embodiments, the metal oxide catalyst component is selected from the group consisting of Zn supported on titania, In supported on zirconia, Ga supported on zirconia, a mixture of In and La supported on zirconia, and a mixture of Ga and La supported on zirconia.

Without being bound by any particular theory, it is believed that the selection of metal oxide catalyst components described herein will provide oxygenated components that can be readily converted by the microporous catalyst components described herein to produce a high concentration of propane in the final product stream.

Without being bound by any particular theory, it is believed that the high acidity of the microporous component allows for the interconversion and hydrogenation of intermediate olefins, leading to a high concentration of propane in the final product stream.

Microporous Catalyst Component

In any of the above embodiments, after the metal oxide catalyst component has been formed-such as, for example, by the methods disclosed above—the metal oxide catalyst component is combined with a microporous catalyst component. The microporous catalyst component is, in embodiments, selected from aluminosilicate molecular sieves having 8-MR pore openings and having a CHA framework type corresponding to the naming convention of the International Zeolite Association (IZA). Examples of molecular sieves having 8-MR pore openings may include, but are not necessarily limited to: CHA embodiments of SSZ-13. Combinations of microporous catalyst components having 8-MR pore openings may also be employed.

As will be discussed in more detail below, the Brönsted acid site concentration of the microporous catalyst component may aid in targeting formation of specific hydrocarbons, such as, for example, propane, over other hydrocarbons, such as, for example, ethane. Accordingly, in embodiments, the Brönsted acid site concentration of the microporous catalyst component is greater than 0.25 millimole per gram (mmol/g), such as greater than 0.30 mmol/g, greater than 0.35 mmol/g, greater than 0.40 mmol/g, greater than 0.45 mmol/g, greater than 0.50 mmol/g, or greater than 0.55 mmol/g. According to embodiments, the maximum Brönsted acid site concentration of the microporous catalyst component is 0.60 mmol/g. Thus, in embodiments, the Brönsted acid site concentration of the microporous catalyst component is from 0.25 mmol/g to 0.60 mmol/g, such as from 0.30 mmol/g to 0.60 mmol/g, from 0.35 mmol/g to 0.60 mmol/g, from 0.40 mmol/g to 0.60 mmol/g, from 0.45 mmol/g to 0.60 mmol/g, from 0.50 mmol/g to 0.60 mmol/g, or from 0.55 mmol/g to 0.60 mmol/g. In embodiments, the Brönsted acid site concentration of the microporous acid component is from 0.25 mmol/g to 0.55 mmol/g, such as from 0.25 mmol/g to 0.50 mmol/g, from 0.25 mmol/g to 0.45 mmol/g, from 0.25 mmol/g to 0.25 mmol/g, from 0.25 mmol/g to 0.35 mmol/g, or from 0.25 mmol/g to 0.30 mmol/g.

In addition to having a high Brönsted acid site concentration—such as those described above—microporous catalyst components according to embodiments also have strong Brönsted acid sites as measured as ammonia desorption peak temperature described herein below (the Brönsted acid site strength is also referred to herein as "T max"). Microporous catalyst components according to embodiments disclosed and described herein have a Brönsted acid site strength measured as $NH_3$— desorption at a rate of 5° C./min in a range from 380° C. to 500° C., such as from 390° C. to 500° C., from 400° C. to 500° C., from 410° C. to 500° C., from 420° C. to 500° C., from 430° C. to 500° C., from 440° C. to 500° C., from 450° C. to 500° C., from 460° C. to 500° C., from 470° C. to 500° C., from 480° C. to 500° C., or from 400° C. to 500° C. In embodiments the microporous catalyst component has a Brönsted acid site strength in a range from 380° C. to 490° C., such as from 380° C. to 480° C., from 380° C. to 470° C., from 380° C. to 460° C., from 380° C. to 450° C., from 380° C. to 440° C., from 380° C. to 430° C., from 380° C. to 420° C., from 380° C. to 410° C., from 380° C. to 400° C., or from 380° C. to 390° C. In some embodiments, the microporous catalyst component has a Brönsted acid site strength in a range from 390° C. to 490° C., such as from 400° C. to 480° C., from 410° C. to 470° C., from 420° C. to 460° C., from 430° C. to 450° C., or about 440° C. It should be understood that any of the above Brönsted acid site strengths may be combined with any of the above Brönsted acid site concentrations described herein.

It should be understood that the microporous catalyst component may have different membered ring pore opening depending on the desired product. For instance, microporous catalyst component having 8-MR to 12-MR pore openings could be used depending on the desired product. However, to produce $C_2$ to $C_5$ paraffins, a microporous catalyst component having 8-MR pore openings is used in embodiments. The metal oxide catalyst component may be added to the microporous catalyst component in the amounts disclosed above.

Preparation Of The Hybrid Catalyst

The non-calcined or calcined metal oxide catalyst component is combined with a microporous catalyst component by any method known to skilled artisans.

The metal oxide catalyst component may, in embodiments, comprise from 9.0 wt % to 91.0 wt % of the hybrid catalyst, such as from 10.0 wt % to 91.0 wt %, from 15.0 wt % to 91.0 wt %, from 20.0 wt % to 91.0 wt %, from 25.0 wt % to 91.0 wt %, from 30.0 wt % to 91.0 wt %, from 35.0 wt % to 91.0 wt %, from 40.0 wt % to 91.0 wt %, from 45.0 wt % to 91.0 wt %, from 50.0 wt % to 91.0 wt %, from 55.0 wt % to 91.0 wt %, from 60.0 wt % to 91.0 wt %, from 65.0 wt % to 91.0 wt %, from 70.0 wt % to 91.0 wt %, from 75.0 wt % to 91.0 wt %, from 80.0 wt % to 91.0 wt %, or from 85.0 wt % to 91.0 wt %. In some embodiments, the metal oxide catalyst component comprises from 9.0 wt % to 85.0 wt %, from 9.0 wt % to 80.0 wt %, from 9.0 wt % to 75.0 wt %, from 9.0 wt % to 70.0 wt %, from 9.0 wt % to 65.0 wt %, from 9.0 wt % to 60.0 wt %, from 9.0 wt % to 55.0 wt %, from 91.0 wt % to 50.0 wt %, from 9.0 wt % to 45.0 wt %, from 9.0 wt % to 40.0 wt %, from 9.0 wt % to 35.0 wt %, from 9.0 wt % to 30.0 wt %, from 9.0 wt % to 25.0 wt %, from 9.0 wt % to 20.0 wt %, or from 9.0 wt % to 15.0 wt %. In some embodiments, the metal oxide catalyst component comprises from 10.0 wt % to 90.0 wt %, from 15.0 wt % to 85.0 wt %, from 20.0 wt % to 80.0 wt %, from 25.0 wt % to 75.0 wt %, from 30.0 wt % to 70.0 wt %, from 35.0 wt % to 65.0 wt %, from 40.0 wt % to 60.0 wt %, or from 45.0 wt % to 55.0 wt %.

Methods for Forming $C_2$ to $C_5$ Paraffins Using the Hybrid Catalyst

After the metal oxide catalyst component has been formed and combined with a microporous catalyst component to form a hybrid catalyst, the hybrid catalyst may be used in methods for converting carbon in a carbon-containing feed stream to $C_2$ to $C_5$ paraffins. Such processes will be described in more detail below.

According to embodiments, a feed stream is fed into a reaction zone, the feed stream comprises hydrogen ($H_2$) gas and a carbon-containing gas selected from carbon monoxide (CO), carbon dioxide ($CO_2$), and combinations thereof. In some embodiments, the $H_2$ gas is present in the feed stream in an amount of from 10 volume percent (vol %) to 90 vol %, based on combined volumes of the $H_2$ gas and the gas selected from CO, $CO_2$, and combinations thereof. The feed stream is contacted with a hybrid catalyst comprising: a microporous catalyst component; and a metal oxide catalyst component that comprises a metal and a support material, the support material comprising at least one oxide of a metal selected from Group 4 of the IUPAC periodic table of elements.

The feed stream is contacted with the hybrid catalyst in the reaction zone under reaction conditions sufficient to form a product stream comprising $C_2$ to $C_5$ paraffins. The reaction conditions comprise a temperature within reaction zone ranging, according to one or more embodiments, from 350° C. to 450° C., such as from 350° C. to 425° C., from 350° C. to 400° C., or from 350° C. to 375° C. In embodiments, the temperature within the reaction zone is from 375° C. to 450° C., from 400° C. to 450° C., or from 425° C. to 450° C. In some embodiments, the temperature within the reaction zone is from 375° C. to 425° C., such as about 400° C.

The reaction conditions also, in embodiments, include a pressure inside the reaction zone of at least 10 bar (1,000 kPa), at least 15 bar (1,500 kPa), at least 20 bar (2,000 kPa), at least 25 bar (2,500 kPa), at least 30 bar (3,000 kPa), at least 35 bar (3,500 kPa), at least 40 bar (4,000 kPa), at least 45 bar (4,500 kPa), at least 50 bar (5,000 kPa), at least 55 bar (5,500 kPa), at least 60 bar (6,000 kPa), at least 65 bar (6,500 kPa), at least 70 bar (7,000 kPa), at least 75 bar (7,500 kPa), at least 80 bar (8,000 kPa), at least 85 bar (8,500 kPa), at least 90 bar (9,000 kPa), at least 95 bar (9,500 kPa), or at least 100 bar (10,000 kPa). In other embodiments, the reaction conditions include a pressure inside the reaction zone that is from 10 bar (1,000 kPa) to 90 bar (9,000 kPa), such as from 15 bar (1,500 kPa) to 85 bar (8,500 kPa), from 20 bar (2,000 kPa) to 80 bar (8,000 kPa), from 25 bar (2,500 kPa) to 75 bar (7,500 kPa), from 30 bar (3,000 kPa) to 70 bar (7,000 kPa), from 35 bar (3,500 kPa) to 65 bar (6,500 kPa), from 40 bar (4,000 kPa) to 60 bar (6,000 kPa), or from 45 bar (4,500 kPa) to 55 bar (5,500 kPa). In some embodiments, the pressure inside the reaction zone is from 20 bar (2,000 kPa) to 60 bar (6,000 kPa).

According to embodiments, the gas hourly space velocity (GHSV) within the reaction zone is from 500 per hour (/h) to 15,000/h, such as from 1,000/h to 14,500/h, from 1,500/h to 14,000/h, from 2,000/h to 13,500/h, from 2,500/h to 13,000/h, from 3,000/h to 12,500/h, from 3,500/h to 12,000/h, from 4,000/h to 11,500/h, from 4,500/h to 11,000/h, from 5,000/h to 10,500/h, from 5,500/h to 10,000/h, from 6,000/h to 9,500/h, from 6,500/h to 9,000/h, from 7,000/h to 8,500/h. or from 7,500/h to 8,000/h. In some embodiments the GHSV within the reaction zone is from 1,800/h to 3,600/h, such as from 2,000/h to 3,600/h, from 2,200/h to 3,600/h, from 2,400/h to 3,600/h, from 2,600/h to 3,600/h, from 2,800/h to 3,600/h, from 3,000/h to 3,600/h, from 3,200/h to 3,600/h, or from 3,400/h to 3,600/h. In some embodiments, the GHSV within the reaction zone is from 1,800/h to 3,400/h, such as from 1,800/h to 3,200/h, from 1,800/h to 3,000/h, from 1,800/h to 2,800/h, from 1,800/h to 2,600/h, from 1,800/h to 2,400/h, from 1,800/h to 2,200/h, or from 1,800/h to 2,000/h. In some embodiments, the GHSV within the reaction is from 2,000/h to 3,400/h, such as from 2,200/h to 3,200/h, from 2,400/h to 3,000/h, or from 2,600/h to 2,800/h.

By using hybrid catalysts disclosed and described herein along with the process conditions disclosed and described herein, high $C_2$ to $C_5$ paraffin fractions and carbon conversion may be achieved. For example, in embodiments the $C_2$ to $C_5$ paraffin fraction as a carbon mole percent of all hydrocarbons is greater than or equal to 60.0 mol %, greater than or equal to 65.0 mol %, greater than or equal to 70.0 mol %, greater than or equal to 75.0 mol %, greater than or equal to 80.0 mol %, greater than or equal to 85.0 mol %, greater than or equal to 90.0 mol %, greater than or equal to 95.0 mol %, greater than or equal to 99.0 mol %, or equal to 100.0 mol %.

In embodiments, using hybrid catalysts disclosed and described herein along with the process conditions disclosed and described herein, carbon conversion can be greater than or equal to 25.0 mol %, such as greater than or equal to 30.0 mol %, greater than or equal to 35.0 mol %, greater than or equal to 40.0 mol %, greater than or equal to 45.0 mol %, greater than or equal to 50.0 mol %, greater than or equal to 55.0 mol %, greater than or equal to 60.0 mol %, greater than or equal to 65.0 mol %, greater than or equal to 70.0 mol %, or greater than or equal to 75.0 mol %. In embodiments, the carbon conversion may be from greater than or equal to 25.0 mol % to 100.0 mol %, such as from 30.0 mol % to 100.0 mol %, from 35.0 mol % to 100.0 mol %, from 40.0 mol % to 100.0 mol %, from 45.0 mol % to 100.0 mol %, from 50.0 mol % to 100.0 mol %, from 55.0 mol % to 100.0 mol %, from 60.0 mol % to 100.0 mol %, from 65.0 mol % to 100.0 mol %, from 70.0 mol % to 100.0 mol %, from 75.0 mol % to 100.0 mol %, from 80.0 mol % to 100.0 mol %, from 85.0 mol % to 100.0 mol %, or from 90.0 mol % to 100.0 mol %.

In addition to good carbon conversion and $C_2$ to $C_5$ paraffin fraction, the combination of metal oxide catalyst components and microporous catalyst components disclosed herein can provide targeted production of certain hydrocarbons. For instance, the combination of metal oxide catalyst components and microporous catalyst components disclosed herein can provide improved production of propane. The two most prevalent paraffins produced in the processes described herein are ethane and propane. Thus, the production of propane is measured herein as a carbon molar ratio found in $C_3$ hydrocarbons to that found in $C_2$ hydrocarbons ($C_3/C_2$) based on the moles of carbon in the $C_3$ hydrocarbons and $C_2$ hydrocarbons. Conventional methods for producing paraffins generally have a relatively low $C_3/C_2$ carbon molar ratios, such as $C_3/C_2$ carbon molar ratios between 1.0 and 2.5. However, methods for producing paraffins disclosed and described herein provides product streams with $C_3/C_2$ carbon molar ratios greater than or equal to 4.0, such as greater than or equal to 4.2, greater than or equal to 4.5, greater than or equal to 4.8, greater than or equal to 5.0, greater than or equal to 5.2, greater than or equal to 5.5, greater than or equal to 5.8, greater than or equal to 6.0, greater than or equal to 6.2, greater than or equal to 6.5, greater than or equal to 6.8, greater than or equal to 7.0, greater than or equal to 7.2, greater than or equal to 7.5, greater than or equal to 7.8, greater than or equal to 8.0, greater than or equal to 8.2, greater than or equal to 8.5, greater than or equal to 8.8, greater than or equal to 9.0, greater than or equal to 9.2, greater than or equal to 8.5, greater than or equal to 9.8, greater than or equal to 10.0, greater than or equal to 10.2, greater than or equal to 10.5, greater than or equal to 10.8, greater than or equal to 11.0, greater than or equal to 11.2, greater than or equal to 11.5, greater than or equal to 11.8, greater than or equal to 12.0, greater than or equal to 12.2, greater than or equal to 12.5, greater than or equal to 12.8, greater than or equal to 13.0, greater than or equal to 13.2, greater than or equal to 13.5, greater than or equal to 13.8, or greater than or equal to 14.0. In some embodiments, the $C_3/C_2$ carbon molar ratio in the product stream is from 4.0 to 16.0, such as from 4.2 to 16.0, from 4.5 to 16.0, from 4.8 to 16.0, from 5.0 to 16.0, from 5.2 to 16.0, from 5.5 to 16.0, from 5.8 to 16.0, from 6.0 to 16.0, from 6.2 to 16.0, from 6.5 to 16.0, from 6.8 to 16.0, from 7.0 to 16.0, from 7.2 to 16.0, from 7.5 to 16.0, from 7.8 to 16.0, from 8.0 to 16.0, from 8.2 to 16.0, from 8.5 to 16.0, from 8.8 to 16.0, from 9.0 to 16.0, from 9.2 to 16.0, from 9.5 to 16.0, from 9.8 to 16.0, from 10.0 to 16.0, from 10.2 to 16.0, from 10.5 to 16.0, from 10.8 to 16.0, from 11.0 to 16.0, from 11.2 to 16.0, from 11.5 to 16.0, from 11.8 to 16.0, from 12.0 to 16.0, from 12.2 to 16.0, from 12.5 to 16.0, from 12.8 to 16.0, from 13.0 to 16.0, from 13.2 to 16.0, from 13.5 to 16.0, from 13.8 to 16.0, from 14.0 to 16.0, from 14.2 to 16.0, from 14.5 to 16.0, from 14.8 to 16.0, from 15.0 to 16.0, from 15.2 to 16.0, from 15.5 to 16.0, or from 15.8 to 16.0. In some embodiments, the $C_3/C_2$ molar ratio in the produce stream is from 4.0 to 15.8, such as from 4.0 to 15.5, from 4.0 to 15.2, from 4.0 to 15.0, from 4.0 to 14.8, from 4.0 to 14.5, from 4.0 to 14.2, from 4.0 to 14.0, from 4.0 to 13.8, from 4.0 to 13.5, from 4.0 to 13.2, from 4.0 to 13.0, from 4.0 to 12.8, from 4.0 to 12.5, from 4.0 to 12.2, from 4.0 to 12.0, from 4.0 to 11.8, from 4.0 to 11.5, from 4.0 to 11.2, from 4.0 to 11.0, from 4.0 to 10.8, from 4.0 to 10.5, from 4.0 to 10.2, from 4.0 to 10.0, from 4.0 to 9.8, from 4.0 to 9.5, from 4.0 to 9.2, from 4.0 to 9.0, from 4.0 to 8.8, from 4.0 to 8.5, from 4.0 to 8.2, from 4.0 to 8.0, from 4.0 to 7.8, from 4.0 to 7.5, from 4.0 to 7.2, from 4.0 to 7.0, from 4.0 to 6.8, from 4.0 to 6.5, from 4.0 to 6.2, from 4.0 to 6.0, from 4.0 to 5.8, from 4.0 to 5.5, from 4.0 to 5.2, from 4.0 to 5.0, from 4.0 to 4.8, from 4.0 to 4.5, or from 4.0 to 4.2.

The amount of propane in the product stream may also be measured as a carbon mole percent of propane in the hydrocarbons in the product stream. In embodiments, the carbon mol % of propane to hydrocarbons in the product stream is greater than or equal to 50.0 mol %, such as greater than or equal to 55.0 mol %, greater than or equal to 60.0 mol %, greater than or equal to 70.0 mol %. In embodiments, the carbon mol % of propane to hydrocarbons in the product stream is from 50.0 mol % to 75.0 mol %, from 55.0 mol % to 75.0 mol %, from 60.0 mol % to 75.0 mol %, or from 65.0 mol % to 75.0 mol %.

This improved propane production was unexpected in view of the literature. For instance, Yang et al., "Design of Efficient Bifunctional Catalysts for Direct Conversion of Syngas Into Lower Olefins Via Methanol/Dimethyl Ether Intermediates," 9 CHEM. SCI. 4708-4718 (2018) discloses using a hybrid catalyst comprising a $Zn/ZrO_2$ metal oxide catalyst component and a SSZ-13 microporous catalyst component for conversion of syngas to olefins. In this reference, SSZ-13 microporous catalyst components with different Brönsted acid site concentrations were combined with a $Zn/ZrO_2$ metal oxide component. At a Brönsted acid site concentration level of about 0.1 mmol/g, the peak olefin selectivity was reported. Upon increasing Brönsted acid site concentration to levels higher than 0.1 mmol/g, more and more saturated products are produced. The breakdown of the $C_2$-$C_5$ hydrocarbon product distribution shows a maximum $C_3/C_2$ ratio of 2.5. There is no disclosure in this reference how to change or manipulate the $C_3/C_2$ ratio in a hybrid catalyst system comprising a $Zn/ZrO_2$ metal oxide catalyst component and a SSZ-13 microporous catalyst component. Further, other literature indicates that increasing the Brönsted acid sites concentration of the microporous catalyst component in a methanol-to-olefins process generally increases the $C_2$ production of the process and decreases the lifetime of the catalyst. However, as provided above and shown in the examples that follow, it was unexpectedly found that the combination of metal oxide catalyst components and microporous catalyst components with high and strong Brönsted acid site concentration described herein, increase the molar ratio of $C_3/C_2$.

EXAMPLES

Embodiments will be further clarified by the following examples.

The conditions for testing the efficacy of the catalyst of the examples and comparative example are measured by placing the hybrid catalyst in a reactor zone and contacting the hybrid catalyst with a feed gas having the conditions shown in Table 1 below:

TABLE 1

| | $H_2$, vol % | CO, vol % | He, vol % | GHSV, $h^{-1}$ | T, °C | P, bar | Time-on-stream [h] |
|---|---|---|---|---|---|---|---|
| Condition 1 | 60 | 30 | 10 | 1200 | 390 | 30 | 70-90 |
| Condition 2 | 67.5 | 22.5 | 10 | 1200 | 390 | 30 | 92-100 |
| Condition 3 | 60 | 30 | 10 | 1200 | 390 | 20 | 80-100 |
| Condition 4 | 67.2 | 22.5 | 10 | 3600 | 390 | 30 | 102-133 |
| Condition 5 | 67.5 | 22.5 | 10 | 9600 | 400 | 30 | 90-115 |
| Condition 6 | 67.5 | 22.5 | 10 | 3000 | 400 | 30 | 120-136 |
| Condition 7 | 67.5 | 22.5 | 10 | 3600 | 400 | 30 | 90-115 |
| Condition 8 | 67.5 | 22.5 | 10 | 2800 | 400 | 30 | 120-136 |
| Condition 9 | 67.5 | 22.5 | 10 | 1800 | 410 | 40 | 100-120 |
| Condition 10 | 67.5 | 22.5 | 10 | 1800 | 410 | 40 | 100-120 |
| Condition 11 | 67.5 | 22.5 | 10 | 1200 | 360 | 30 | 40-60 |
| Condition 12 | 67.5 | 22.5 | 10 | 1200 | 350 | 30 | 40-60 |

Example 1

A supported metal oxide catalyst component of $Zn/TiO_2$ was prepared by an incipient wetness impregnation method. A stock solution of zinc (II) nitrate hexahydrate with C=2.0 M in DI water was prepared. Then, 1.835 ml of the stock solution was mixed with 1.164 ml of DI water to obtain 3.00 ml of the impregnation solution. Subsequently, 1489.35 mg of 60-80 mesh size $TiO_2$ support (NORPRO ST61120, BET surface area=130 $m^2/g$, 100% anatase phase (measured by XRD), pore volume=0.57 ml/g (measured by DI water)) was weighed and placed into a glass vial. After that, 848.9 µl of the impregnation solution were added dropwise to the support while constantly shaking. After impregnation, the catalyst was dried at 120° C. in an oven (static air) and calcined using the following program: heat from room temperature to 120° C. at 2° C./min; dwell at 120° C. for 2 hours; heat from 120° C. to 400° C. at 3° C./min; dwell at 400° C. for 4 hours; cool down to room temperature in 2 hours. After calcination, the catalyst was re-sieved to 60-80 mesh size to remove fine particles.

The metal oxide catalyst component has the following elemental composition (measured by XRF): 2.02 wt % Zn, 57.74 wt % Ti, 0.151 wt % S and 0.05 wt % P, balance—oxygen.

The hybrid catalyst was then prepared as follows.

The microporous catalyst component of SSZ-13 ($SiO_2/Al_2O_3$=25 mol/mol) with a Brönsted acid site concentration of 0.43 mmol/g (Tmax=417° C.) (measured by $NH_3$—temperature programmed desorption) was used. The microporous catalyst component has the following elemental composition (measure by XRF): 3.3 wt % Al, 43.8 wt % Si, balance—oxygen. The level of impurities present in the microporous catalyst component was determined by ICP technique: 17 ppm Cr, 89 ppm Fe, 1 ppm Mo, and 12 ppm Ni. BET surface area and micropore volume determined from $N_2$ physisorption were 643 $m^2/g$ and 0.286 $cm^3/g$, respectively. The microporous catalyst component was prepared according to conventionally known procedures available in literature.

Subsequently, 150 µL of the metal oxide catalyst component (89.8 mg, 60-80 mesh size) were mixed with 250 µL of SSZ-13 (100.7 mg, 60-80 mesh size) and shaken for 30 sec until well mixed.

The resulting conversion and selectivity achieved is shown in Table 2 below:

TABLE 2

| | Conv., Cmol % | Selectivity, C mol % | | | | | |
|---|---|---|---|---|---|---|---|
| | | $CH_4$ | Ethane | Propane | $C_4$ paraffins | $C_5$ paraffins | Ethylene |
| Condition 1 | 33.8 | 6.0 | 3.8 | 41.4 | 5.3 | 0 | 0.7 |
| Condition 2 | 36.7 | 7.4 | 4.0 | 43.5 | 5.7 | 0 | 0.9 |

| | Selectivity, C mol % | | | | | $C_3$ fraction in $C_1$-$C_5$ hydrocarbons Cmol % |
|---|---|---|---|---|---|---|
| | Propylene | $C_4$ Olefins | $C_5$ Olefins | $CO_2$ | Oxygenates | |
| Condition 1 | 0 | 0.11 | 0 | 42.5 | 0 | 72.0 |
| Condition 2 | 0 | 0.06 | 0 | 38.4 | 0 | 70.6 |

The productivity and selectivity of $C_2$ to $C_5$ paraffins achieved is shown in Table 3 below:

TABLE 3

| | Productivity, g/kg_cat/h | |
|---|---|---|
| | $C_2$-$C_5$ paraffins | Propane |
| Condition 1 | 79.5 | 65.1 |
| Condition 2 | 72.3 | 59.0 |

Example 2

A supported metal oxide catalyst component of Zn/TiO$_2$ was prepared by an incipient wetness impregnation method. A stock solution of zinc (II) nitrate hexahydrate with C=2.0 M in DI water was prepared. Then, 9.18 ml of the stock solution were mixed with 7.92 ml of DI water to obtain 17.1 ml of the impregnation solution. Subsequently, 20000 mg of 60-80 mesh size TiO$_2$ support (NORPRO ST61120, BET surface area=130 m$^2$/g, 100% anatase phase (measured by XRD), pore volume=0.57 ml/g (measured by DI water)) was weighed and placed into a glass vial. After that, 11.4 ml of the impregnation solution were added dropwise to the support while constantly shaking. After impregnation, the metal oxide catalyst component was dried at 120° C. in an oven (static air) and calcined using the following program: heating from room temperature to 120° C. at 2° C./min; dwell at 120° C. for 2 hours; heat from 120° C. to 400° C. at 3° C./min; dwell at 400° C. for 4 hours; cool down to room temperature in 2 hours. After calcination, the catalyst was re-sieved to 60-80 mesh size to remove fine particles.

The catalyst has the following elemental composition (measured by XRF): 4.03 wt % Zn, 55.65 wt % Ti, 0.123 wt % S and 0.05 wt % P, other elements (Zr, Nb)<0.5 wt %, balance—oxygen.

The hybrid catalyst was prepared as follows.

The SSZ-13 (SiO$_2$/Al$_2$O$_3$=25 mol/mol) of Example 1 was used as the microporous catalyst component. 150 μL of the metal oxide catalyst component (91.2 mg, 60-80 mesh size) were mixed with 250 μL of SSZ-13 (102.0 mg, 60-80 mesh size) and shaken for 30 see until well mixed.

The resulting conversion and selectivity achieved is shown in Table 4 below:

TABLE 4

| | Conv., Cmol % | Selectivity, Cmol % | | | | | |
|---|---|---|---|---|---|---|---|
| | | $CH_4$ | Ethane | Propane | $C_4$ paraffins | $C_5$ paraffins | Ethylene |
| Condition 1 | 29.9 | 5.5 | 3.8 | 43.8 | 5.5 | 0 | 0.8 |
| Condition 2 | 32.5 | 7.3 | 4.3 | 45.1 | 5.7 | 0 | 1.2 |

| | Selectivity, Cmol % | | | | | $C_3$ fraction in $C_1$-$C_5$ hydrocarbons Cmol % |
|---|---|---|---|---|---|---|
| | Propylene | $C_4$ Olefins | $C_5$ Olefins | $CO_2$ | Oxygenates | |
| Condition 1 | 0 | 0 | 0 | 40.5 | 0 | 73.6 |
| Condition 2 | 0 | 0 | 0 | 36.4 | 0 | 70.9 |

The productivity and selectivity of $C_2$ to $C_5$ paraffins achieved is shown in Table 5 below:

TABLE 5

|  | Productivity, g/kg_cat/h | |
| --- | --- | --- |
|  | $C_2$-$C_5$ paraffins | Propane |
| Condition 1 | 74.2 | 61.0 |
| Condition 2 | 64.0 | 52.2 |

Example 3

A supported metal oxide catalyst component of In/ZrO$_2$ was prepared by a rotavapor method. A stock solution of indium (III) nitrate hydrate with C=1.534 M in DI water was prepared. Then, 893.5 µl of the stock solution were mixed with 10.0 ml of DI water to obtain 10.893 ml of the precursor solution. Subsequently, 6230 mg of 60-80 size ZrO$_2$ support (NORPRO, SZ31164, BET surface area=98 m2/g, 100% monoclinic phase by XRD) were placed in a round-bottom flask for Rotavapor followed by 10.893 ml of the precursor solution. The flask was set to rotation and vacuum was on. DI water was removed under vacuum until the dry powder was obtained. The as-prepared material was dried at 120° C. in an oven (static air) and calcined using the following program: heating from room temperature to 120° C. at 2° C./min; dwell at 120° C. for 2 hours; heated from 120° C. to 550° C. at 3° C./min; dwell at 550° C. for 4 hours, cooled down to room temperature in 2 hours. After calcination, the metal oxide catalyst component was re-sieved to 60-80 mesh size to remove fine particles.

The metal oxide catalyst component has the following elemental composition (measured by XRF): 2.33 wt % In, 69.5 wt % Zr, 2.43 wt % Hf, balance—oxygen.

The hybrid catalyst was prepared as follows.

The SSZ-13 (SiO$_2$/Al$_2$O$_3$=25 mol/mol) of Example 1 was used as the microporous catalyst component. 150 µL of the metal oxide catalyst component (147.6 mg, 60-80 mesh size) were mixed with 250 µL of SSZ-13 (100.7 mg, 60-80 mesh size) and shaken for 30 see until well mixed.

The resulting conversion and selectivity achieved is shown in Table 6 below:

TABLE 6

| | Conv., Cmol % | Selectivity, Cmol % | | | | | |
| --- | --- | --- | --- | --- | --- | --- | --- |
| | | CH$_4$ | Ethane | Propane | $C_4$ paraffins | $C_5$ paraffins | Ethylene |
| Condition 1 | 67.7 | 3.7 | 5.3 | 34.1 | 2.5 | 0 | 1.2 |
| Condition 2 | 75.3 | 4.0 | 4.8 | 45.0 | 3.8 | 0 | 0.9 |
| Condition 3 | 55.5 | 3.9 | 6.0 | 29.4 | 1.1 | 0 | 1.7 |
| Condition 4 | 50.7 | 4.0 | 4.0 | 43.7 | 3.2 | 0 | 1.6 |

| | Selectivity, Cmol % | | | | | |
| --- | --- | --- | --- | --- | --- | --- |
| | Propylene | $C_4$ Olefins | $C_5$ Olefins | $CO_2$ | Oxygenates | $C_3$ fraction in $C_1$-$C_5$ hydrocarbons Cmol % |
| Condition 1 | 5.4 | 1.3 | 0 | 46.5 | 0 | 73.4 |
| Condition 2 | 0 | 0.5 | 0 | 41.0 | 0 | 76.2 |
| Condition 3 | 8.3 | 1.6 | 0 | 47.8 | 0 | 72.3 |
| Condition 4 | 0 | 0.8 | 0 | 42.5 | 0.1 | 76.1 |

The productivity and selectivity of $C_2$ to $C_5$ paraffins achieved is shown in Table 7 below:

TABLE 7

| | Productivity, g/kg_cat/h | |
|---|---|---|
| | $C_2$-$C_5$ paraffins | Propane |
| Condition 1 | 91.7 | 74.4 |
| Condition 2 | 112 | 94.0 |
| Condition 3 | 77.3 | 61.9 |
| Condition 4 | 224.5 | 192.5 |

Example 4

The metal oxide catalyst component of Example 3 was used (In/ZrO$_2$) and the microporous catalyst component of Example 1 was used (SSZ-13 (SiO$_2$/Al$_2$O$_3$=25 mol/mol).

50 μL of the metal oxide catalyst component (50 mg, 60-80 mesh size) were mixed with 250 μL of the microporous catalyst component (100 mg, 60-80 mesh size) and shaken for 30 see until well mixed. Then, 100 μL of the as-prepared mixture were taken to yield a composite catalyst containing about 17 μL of In/ZrO$_2$ (about 15 mg) and 83 μL of SSZ-13 (about 35 mg).

The resulting conversion and selectivity achieved is shown in Table 8 below:

TABLE 8

| | Conv., Cmol % | Selectivity, Cmol % | | | | | |
|---|---|---|---|---|---|---|---|
| | | CH$_4$ | Ethane | Propane | $C_4$ paraffins | $C_5$ paraffins | Ethylene |
| Condition 5 | 15.8 | 9.4 | 3.8 | 34.8 | 5.0 | 0 | 3.5 |
| Condition 6 | 34.9 | 10.2 | 5.4 | 33.9 | 3.9 | 0 | 1.6 |

| | Selectivity, Cmol % | | | | | |
|---|---|---|---|---|---|---|
| | Propylene | $C_4$ Olefins | $C_5$ Olefins | CO$_2$ | Oxygenates | $C_3$ fraction in $C_1$-$C_5$ hydrocarbons Cmol % |
| Condition 5 | 0 | 0.5 | 0 | 43.0 | 0 | 61.0 |
| Condition 6 | 0 | 0.11 | 0 | 44.8 | 0 | 61.5 |

The productivity and selectivity of $C_2$ to $C_5$ paraffins achieved is shown in Table 9 below:

TABLE 9

| | Productivity, g/kg_cat/h | |
|---|---|---|
| | $C_2$-$C_5$ paraffins | Propane |
| Condition 5 | 195.6 | 156.3 |
| Condition 6 | 134.7 | 105.4 |

Example 5

A supported metal oxide catalyst component of Ga/ZrO$_2$ was prepared by an incipient wetness impregnation method. A stock solution of gallium (III) nitrate hydrate with C=1.553 M in DI water was prepared. Then, 515.1 μl ml of the stock solution were mixed with 244.9 μl of DI water to obtain 760 μl of the impregnation solution. Subsequently, 1323 mg of 60-80 mesh size ZrO$_2$ support (NORPRO, SZ31164, BET surface area=98 m$^2$/g, 100% monoclinic phase (measured by XRD), pore volume=0.38 ml/g (measured by DI water)) was weighed and placed into a glass vial. After that, 502 μl of the impregnation solution were added dropwise to the support while constantly shaking. After impregnation, the catalyst was dried at 120° C. in an oven (static air) and calcined using the following program: heated from room temperature to 120° C. at 2° C./min; dwell at 120° C. for 2 hours; heated from 120° C. to 550° C. at 3° C./min; dwell at 550° C. for 4 hours; cooled down to room temperature in 2 hours. After calcination, the catalyst was re-sieved to 60-80 mesh size to remove fine particles.

The hybrid catalyst was prepared as follows.

The microporous catalyst component of Example 1 was used (SSZ-13 (SiO$_2$/Al$_2$O$_3$=25 mol/mol). 100 μL of the metal oxide catalyst component (93 mg, 60-80 mesh size) were mixed with 200 μL of SSZ-13 (87.5 mg, 60-80 mesh size) and shaken for 30 see until well mixed.

The resulting conversion and selectivity achieved is shown in Table 10 below:

TABLE 10

| | Conv., Cmol % | Selectivity, Cmol % | | | | | |
|---|---|---|---|---|---|---|---|
| | | $CH_4$ | Ethane | Propane | $C_4$ paraffins | $C_5$ paraffins | Ethylene |
| Condition 7 | 37.3 | 3.9 | 3.3 | 47.8 | 6.9 | 0 | 1.5 |
| Condition 8 | 41.4 | 4.1 | 3.4 | 47.1 | 6.6 | | 1.3 |

| | Selectivity, Cmol % | | | | | |
|---|---|---|---|---|---|---|
| | Propylene | $C_4$ Olefins | $C_5$ Olefins | $CO_2$ | Oxygenates | $C_3$ fraction in $C_1$-$C_5$ hydrocarbons Cmol % |
| Condition 7 | 0.3 | 0 | 0 | 36.4 | 0 | 75.0 |
| Condition 8 | 0 | 0.3 | 0 | 37.0 | 0 | 75.0 |

The productivity and selectivity of $C_2$ to $C_5$ paraffins achieved is shown in Table 11 below:

TABLE 11

| | Productivity, g/kg_cat/h | |
|---|---|---|
| | $C_2$-$C_5$ paraffins | Propane |
| Condition 7 | 191.9 | 158.1 |
| Condition 8 | 163.9 | 135.0 |

Example 6

A supported metal oxide catalyst component of In—La/$ZrO_2$ was prepared by an incipient wetness impregnation method. A stock solution of indium (III) nitrate hydrate with C=1.50 M in DI water was prepared. A stock solution of lanthanum (III) nitrate hexahydrate with C=0.623 M in DI water was prepared. The impregnation solution (8.2 ml) was prepared by mixing 2.933 ml of the indium stock solution, 2118.8 ml of the lanthanum stock solution and 3.147 ml of DI water. Then, 15 g of 60-80 mesh size $ZrO_2$ support (NORPRO, SZ31108, BET surface area=84 $m^2$/g, 100% monoclinic phase (measured by XRD), pore volume=0.41 ml/g (measured by DI water)) was weighed and placed into a glass vial. After that, 6.15 ml of the impregnation solution were added dropwise to the support while constantly shaking. After impregnation, the catalyst was dried at 120° C. in an oven (static air) and calcined using the following program: heated from room temperature to 120° C. at 2° C./min; dwell at 120° C. for 2 hours; heated from 120° C. to 550° C. at 3° C./min; dwell at 550° C. for 4 hours; cooled down to room temperature in 2 hours. After calcination, the catalyst was re-sieved to 60-80 mesh size to remove fine particles.

The catalyst has the following elemental composition (measured by XRF): 1.88 wt % In, 0.758 wt % La, 69.4 wt % Zr, 2.28 wt % Hf, balance—oxygen.

The hybrid catalyst was prepared as follows.

The microporous catalyst component of Example 1 was used (SSZ-13 ($SiO_2$/$Al_2O_3$=25 mol/mol). 150 μL of the metal oxide catalyst component (144.6 mg, 60-80 mesh size) were mixed with 250 μL of SSZ-13 (94.7 mg, 60-80 mesh size) and shaken for 30 see until well mixed.

The resulting conversion and selectivity achieved is shown in Table 12 below:

TABLE 12

| | Conv., Cmol % | Selectivity, Cmol % | | | | | |
|---|---|---|---|---|---|---|---|
| | | $CH_4$ | Ethane | Propane | $C_4$ paraffins | $C_5$ paraffins | Ethylene |
| Condition 9 | 74.5 | 2.8 | 3.3 | 49.0 | 6.8 | 0 | 0.9 |

| | Selectivity, Cmol % | | | | | |
|---|---|---|---|---|---|---|
| | Propylene | $C_4$ Olefins | $C_5$ Olefins | $CO_2$ | Oxygenates | $C_3$ fraction in $C_1$-$C_5$ hydrocarbons Cmol % |
| Condition 9 | 0 | 1.4 | 0 | 35.5 | 0.1 | 76.2 |

The productivity and selectivity of $C_2$ to $C_5$ paraffins achieved is shown in Table 13 below:

TABLE 13

| | Productivity, g/kg_cat/h | |
|---|---|---|
| | $C_2$-$C_5$ paraffins | Propane |
| Condition 9 | 204.0 | 169.0 |

Example 7

The metal oxide catalyst component of Example 6 was used (In—La/$ZrO_2$), and the microporous catalyst component of Example 1 was used (SSZ-13 $SiO_2/Al_2O_3$=25 mol/mol). 250 µL of the metal oxide catalyst component (In—La/$ZrO_2$; 238.2 mg, 60-80 mesh size) were mixed with 150 µL of the microporous catalyst component (SSZ-13; 58.5 mg, 60-80 mesh size) and shaken for 30 see until well mixed.

The resulting conversion and selectivity achieved is shown in Table 14 below:

TABLE 14

| | Conv., Cmol % | Selectivity, Cmol % | | | | | |
|---|---|---|---|---|---|---|---|
| | | $CH_4$ | Ethane | Propane | $C_4$ paraffins | $C_5$ paraffins | Ethylene |
| Condition 9 | 76.5 | 3.4 | 5.4 | 35.3 | 2.4 | 0 | 1.9 |

| | Selectivity, Cmol % | | | | | |
|---|---|---|---|---|---|---|
| | Propylene | $C_4$ Olefins | $C_5$ Olefins | $CO_2$ | Oxygenates | $C_3$ fraction in $C_1$-$C_5$ hydrocarbons Cmol % |
| Condition 9 | 9.7 | 5.6 | 0 | 36.0 | 0.1 | 70.5 |

The productivity and selectivity of $C_2$ to $C_5$ paraffins achieved is shown in Table 15 below:

TABLE 15

| | Productivity, g/kg_cat/h | |
|---|---|---|
| | $C_2$-$C_5$ paraffins | Propane |
| Condition 9 | 120.4 | 98.4 |

Example 8

The metal oxide catalyst component of Example 6 was used (In—La/$ZrO_2$). The microporous catalyst component was SSZ-13 ($SiO_2/Al_2O_3$=30 mol/mol) with Brönsted acid site concentration of 0.49 mmol/g (Tmax=420° C.) (measured by $NH_3$— temperature programmed desorption). The microporous catalyst component has the following elemental composition (measured by XRF): 2.84 wt % Al, 44.2 wt % Si, balance—oxygen. The level of impurities present in the microporous catalyst component (measured by ICP technique): 20 ppm Fe, (Cr, Mo, Ni—below detection limit). BET surface area and micropore volume determined from $N_2$ physisorption were 654 m²/g and 0.2887 cm³/g. The microporous catalyst component was prepared according conventionally known procedures available in literature.

The hybrid catalyst was prepared as follows.

150 µL of the metal oxide catalyst component (141.8 mg, 60-80 mesh size) were mixed with 250 µL of the microporous catalyst component (84.3 mg, 60-80 mesh size) and shaken for 30 see until well mixed.

The resulting conversion and selectivity achieved is shown in Table 16 below:

TABLE 16

| | Conv., Cmol % | Selectivity, Cmol % | | | | |
|---|---|---|---|---|---|---|
| | | $CH_4$ | Ethane | Propane | $C_4$ paraffins | $C_5$ paraffins | Ethylene |
| Condition 9 | 74.2 | 3.0 | 2.6 | 48.2 | 7.5 | 0 | 1.0 |

| | Selectivity, Cmol % | | | | | $C_3$ fraction in $C_1$-$C_5$ hydrocarbons Cmol % |
|---|---|---|---|---|---|---|
| | Propylene | $C_4$ Olefins | $C_5$ Olefins | $CO_2$ | Oxygenates | |
| Condition 9 | 0 | 1.7 | 0 | 35.8 | 0.1 | 75.3 |

The productivity and selectivity of $C_2$ to $C_5$ paraffins achieved is shown in Table 17 below:

TABLE 17

| | Productivity, g/kg_cat/h | |
|---|---|---|
| | $C_2$-$C_5$ paraffins | Propane |
| Condition 9 | 212.2 | 175.4 |

Example 9

The metal oxide catalyst component of Example 6 was used (In—La/$ZrO_2$), and the microporous catalyst component of Example 8 was used (SSZ-13 $SiO_2$/$Al_2O_3$=30 mol/mol). 250 µL of the metal oxide catalyst component (In—La/$ZrO_2$; 232.3 mg, 60-80 mesh size) were mixed with 150 µL of the microporous catalyst component (SSZ-13; 53.0 mg, 60-80 mesh size) and shaken for 30 see until well mixed.

The resulting conversion and selectivity achieved is shown in Table 18 below:

TABLE 18

| | Conv., Cmol % | Selectivity, Cmol % | | | | |
|---|---|---|---|---|---|---|
| | | $CH_4$ | Ethane | Propane | $C_4$ paraffins | $C_5$ paraffins | Ethylene |
| Condition 9 | 80.9 | 2.5 | 4.0 | 43.6 | 4.4 | 0 | 1.4 |

| | Selectivity, Cmol % | | | | | $C_3$ fraction in $C_1$-$C_5$ hydrocarbons Cmol % |
|---|---|---|---|---|---|---|
| | Propylene | $C_4$ Olefins | $C_5$ Olefins | $CO_2$ | Oxygenates | |
| Condition 9 | 5.7 | 4.0 | 0 | 34.1 | 0.1 | 75.0 |

The productivity and selectivity of $C_2$ to $C_5$ paraffins achieved is shown in Table 19 below:

TABLE 19

| | Productivity, g/kg_cat/h | |
| --- | --- | --- |
| | $C_2$-$C_5$ paraffins | Propane |
| Condition 9 | 161.3 | 135.2 |

Example 10

A supported metal oxide catalyst component of Ga—La/ $ZrO_2$ was prepared by an incipient wetness impregnation method. A stock solution of gallium (III) nitrate hydrate with C=2.0 M in DI water was prepared. A stock solution of lanthanum (III) nitrate hexahydrate with C=0.623 M in DI water was prepared. The impregnation solution (8.2 ml) was prepared by mixing 4.0 ml of the gallium stock solution, 3.852 ml of the lanthanum stock solution, and 0.3477 ml of DI water to obtain 8.2 ml of the impregnation solution. Then, 15 g of 60-80 mesh size $ZrO_2$ support (NORPRO, SZ31108, BET surface area=84 $m^2$/g, 100% monoclinic phase (measured by XRD), pore volume=0.41 ml/g (measured by DI water)) was weighed and placed into a glass vial. After that, 6.15 ml of the impregnation solution were added dropwise to the support while constantly shaking. After impregnation, the catalyst was dried at 120° C. in an oven (static air) and calcined using the following program: heated from room temperature to 120° C. at 2° C./min; dwell at 120° C. for 2 hours; heated from 120° C. to 550° C. at 3° C./min; dwell at 550° C. for 4 hours; cooled down to room temperature in 2 hours. After calcination, the catalyst was re-sieved to 60-80 mesh size to remove fine particles.

The catalyst has the following elemental composition (measured by XRF): 2.0 wt % Ga, 1.34 wt % La, 68.5 wt % Zr, 2.25 wt % Hf (balance—oxygen).

The hybrid catalyst was prepared as follows.

The microporous catalyst component of Example 1 was used (SSZ-13 ($SiO_2$/$Al_2O_3$=25 mol/mol). 150 μL of the metal oxide catalyst component (141.5 mg, 60-80 mesh size) were mixed with 250 μL of the microporous catalyst component (95.2 mg, 60-80 mesh size) and shaken for 30 see until well mixed.

The resulting conversion and selectivity achieved is shown in Table 20 below:

TABLE 20

| | Conv., Cmol % | Selectivity, Cmol % | | | | |
| --- | --- | --- | --- | --- | --- | --- |
| | | $CH_4$ | Ethane | Propane | $C_4$ paraffins | $C_5$ paraffins | Ethylene |
| Condition 10 | 62.7 | 3.1 | 3.0 | 50.4 | 7.3 | 0 | 0.8 |

| | Selectivity, Cmol % | | | | | |
| --- | --- | --- | --- | --- | --- | --- |
| | Propylene | $C_4$ Olefins | $C_5$ Olefins | $CO_2$ | Oxygenates | $C_3$ fraction in $C_1$-$C_5$ hydrocarbons Cmol % |
| Condition 10 | 0 | 0.7 | 0 | 34.8 | 0.06 | 77.3 |

The productivity and selectivity of $C_2$ to $C_5$ paraffins achieved is shown in Table 21 below:

TABLE 21

| | Productivity, g/kg_cat/h | |
|---|---|---|
| | $C_2$-$C_5$ paraffins | Propane |
| Condition 10 | 177.3 | 147.4 |

Example 11

The metal oxide catalyst component of Example 6 was used (In—La/ZrO$_2$), and the microporous catalyst component of Example 1 was used (SSZ-13 SiO$_2$/Al$_2$O$_3$=25 mol/mol). 100 µL of the metal oxide catalyst component (In—La/ZrO$_2$; 95.7 mg, 60-80 mesh size) were mixed with 300 µL of the microporous catalyst component (SSZ-13; 122.7 mg, 60-80 mesh size) and shaken for 30 sec until well mixed.

The resulting conversion and selectivity achieved is shown in Table 22 below:

TABLE 22

| | Conv., Cmol % | Selectivity, Cmol % | | | | | |
|---|---|---|---|---|---|---|---|
| | | CH$_4$ | Ethane | Propane | $C_4$ paraffins | $C_5$ paraffins | Ethylene |
| Condition 11 | 35.6 | 3.0 | 2.9 | 45.4 | 5.7 | 0 | 0.6 |
| Condition 12 | 63.8 | 2.5 | 2.2 | 44.3 | 6.4 | 0 | 0.4 |

| | Selectivity, Cmol % | | | | $C_3$ fraction in $C_1$-$C_5$ hydrocarbons Cmol % |
|---|---|---|---|---|---|
| | Propylene | $C_4$ Olefins | $C_5$ Olefins | CO$_2$ | Oxygenates | |
| Condition 11 | 0 | 0 | 0 | 42.4 | 0 | 78.8 |
| Condition 12 | 0 | 0.2 | 0 | 43.9 | 0 | 79.0 |

The productivity and selectivity of $C_2$ to $C_5$ paraffins achieved is shown in Table 23 below:

TABLE 23

| | Productivity, g/kg_cat/h | |
|---|---|---|
| | $C_2$-$C_5$ paraffins | Propane |
| Condition 11 | 62.6 | 52.7 |
| Condition 12 | 112.4 | 94.0 |

Example 12

A supported metal oxide catalyst component of Zn/ZrO$_2$ was prepared by an incipient wetness impregnation method. A stock solution of zinc (II) nitrate hexahydrate with C=1.4726 M in DI water was prepared. A stock solution of lanthanum (III) nitrate hexahydrate with C=0.623 M in DI water was prepared. The impregnation solution (8.0 ml) was prepared by mixing 4.753 ml of the zinc stock solution with 3.246 ml of DI water obtain 8.0 ml of the impregnation solution. Then, 10 g of 60-80 mesh size ZrO$_2$ support (NORPRO, SZ31164, BET surface area=98 m$^2$/g, 100% monoclinic phase by XRD, pore volume=0.40 ml/g measured by DI water) was weighed and placed into a glass vial. After that, 4.0 ml of the impregnation solution were added dropwise to the support while constantly shaking. After impregnation, the catalyst was dried at 120° C. in the oven (static air) and calcined using the following program: heated from room temperature to 120° C. at 2° C./min; dwell at 120° C. for 2 hours; heated from 120° C. to 550° C. at 2° C./min; dwell at 550° C. for 4 hours; cooled down to room temperature in 2 hours. After calcination, the catalyst was re-sieved to 60-80 mesh size to remove fine particles.

The mixed oxide has the following elemental composition (measured by XRF): 2.18 wt % Zn, 69.62 wt % Zr, 2.35 wt % Hf, balance—oxygen.

The hybrid catalyst was prepared as follows.

The microporous catalyst component of Example 1 was used (SSZ-13 (SiO$_2$/Al$_2$O$_3$=25 mol/mol). 100 µL of the metal oxide catalyst component (92.0 mg, 60-80 mesh size) were mixed with 300 µL of the microporous catalyst component (122.1 mg, 60-80 mesh size) and shaken for 30 sec until well mixed.

The resulting conversion and selectivity achieved is shown in Table 24 below:

TABLE 24

| | Conv., Cmol % | Selectivity, Cmol % | | | | | |
|---|---|---|---|---|---|---|---|
| | | $CH_4$ | Ethane | Propane | $C_4$ paraffins | $C_5$ paraffins | Ethylene |
| Condition 11 | 38.1 | 4.2 | 3.4 | 44.3 | 6.3 | 0 | 0.8 |

| | Selectivity, Cmol % | | | | | |
|---|---|---|---|---|---|---|
| | Propylene | $C_4$ Olefins | $C_5$ Olefins | $CO_2$ | Oxygenates | $C_3$ fraction in $C_1$-$C_5$ hydrocarbons Cmol % |
| Condition 11 | 0 | 0 | 0 | 40.9 | 0 | 75.0 |

The productivity and selectivity of $C_2$ to $C_5$ paraffins achieved is shown in Table 25 below:

TABLE 25

| | Productivity, g/kg_cat/h | |
|---|---|---|
| | $C_2$-$C_5$ paraffins | Propane |
| Condition 11 | 68.5 | 56.2 |

Comparative Example 1

The metal oxide catalyst component of Example 6 was used. The microporous catalyst component was SAPO-34 made in accordance with the procedure outlined in U.S. Pat. No. 4,440,871 with a Brönsted acid site concentration of 0.75 mmol/g (Tmax=345° C. (measured by $NH_3$— temperature programmed desorption). BET surface area and micropore volume determined from $N_2$ physisorption were 571 m²/g and 0.262 cm³/g, respectively.

The hybrid catalyst was prepared as follows.

The elemental composition of the SAPO-34 microporous catalyst component (measured by XRF) was: 21.2 wt % P, 22.3 wt % Al, 4.3 wt % Si, balance—oxygen. 150 μL of the metal oxide catalyst component (146.7 mg, 60-80 mesh size) were mixed with 250 μL of the microporous catalyst component (140.4 mg, 60-80 mesh size) and shaken for 30 see until well mixed.

The resulting conversion and selectivity achieved is shown in Table 26 below:

TABLE 26

| | Conv., Cmol % | Selectivity, Cmol % | | | | | |
|---|---|---|---|---|---|---|---|
| | | $CH_4$ | Ethane | Propane | $C_4$ paraffins | $C_5$ paraffins | Ethylene |
| Condition 9 | 78.4 | 1.2 | 3.8 | 16.5 | 2.3 | 0.05 | 4.9 |

| | Selectivity, Cmol % | | | | | |
|---|---|---|---|---|---|---|
| | Propylene | $C_4$ Olefins | $C_5$ Olefins | $CO_2$ | Oxygenates | $C_3$ fraction in $C_1$-$C_5$ hydrocarbons Cmol % |
| Condition 9 | 25.0 | 11.7 | 0.01 | 34.5 | 0.03 | 63.4 |

The productivity and selectivity of $C_2$ to $C_5$ paraffins achieved is shown in Table 27 below:

TABLE 27

| | Productivity, g/kg_cat/h | |
| --- | --- | --- |
| | $C_2$-$C_5$ paraffins | Propane |
| Condition 9 | 67.11 | 49 |

Comparative Example 2

The metal oxide catalyst component of Example 6 was used. The microporous catalyst component was SAPO-34 as used in Comparative Example 1.

The hybrid catalyst was prepared as follows.

100 µL of the metal oxide catalyst component (97.2 mg, 60-80 mesh size) were mixed with 300 µL of the microporous catalyst component (181.3 mg, 60-80 mesh size) and shaken for 30 sec until well mixed.

The resulting conversion and selectivity achieved is shown in Table 28 below:

TABLE 28

| | Conv., Cmol % | Selectivity, Cmol % | | | | | |
| --- | --- | --- | --- | --- | --- | --- | --- |
| | | $CH_4$ | Ethane | Propane | $C_4$ paraffins | $C_5$ paraffins | Ethylene |
| Condition 11 | 23.8 | 13.3 | 5.0 | 16.7 | 1.3 | 0 | 3.3 |
| Condition 12 | 23.0 | 10.9 | 3.7 | 9.9 | 0.5 | 0 | 2.6 |

| | Selectivity, Cmol % | | | | $C_3$ fraction in $C_1$-$C_5$ hydrocarbons Cmol % |
| --- | --- | --- | --- | --- | --- |
| | Propylene | $C_4$ Olefins | $C_5$ Olefins | $CO_2$ | Oxygenates | |
| Condition 11 | 1.7 | 0.65 | 0 | 42.3 | 16.8 | 42.4 |
| Condition 12 | 1.9 | 0.68 | 0 | 39.0 | 30.8 | 39.0 |

The productivity and selectivity of $C_2$ to $C_5$ paraffins achieved is shown in Table 29 below:

TABLE 29

| | Productivity, g/kg_cat/h | |
| --- | --- | --- |
| | $C_2$-$C_5$ paraffins | Propane |
| Condition 11 | 13.6 | 9.7 |
| Condition 12 | 8.4 | 5.9 |

Comparative Example 3

The metal oxide catalyst component was a commercially available Cu-based methanol synthesis catalyst (HiFuel™ R120) that has a Cu content of 51 wt %, a Zn content of 20 wt %, and an Al content of 5 wt %. The catalyst was crushed and sieved to 60-80 mesh size.

The microporous catalyst components of Example 1 was used. 100 µL of the metal oxide catalyst component (98.2 mg, 60-80 mesh size) were mixed with 300 µL of the microporous catalyst component (121.3 mg, 60-80 mesh size) and shaken for 30 sec until well mixed The resulting conversion and selectivity achieved is shown in Table 30 below:

TABLE 30

| | Conv., Cmol % | Selectivity, Cmol % | | | | | |
| --- | --- | --- | --- | --- | --- | --- | --- |
| | | $CH_4$ | Ethane | Propane | $C_4$ paraffins | $C_5$ paraffins | Ethylene |
| Condition 11 | 82.0 | 3.8 | 18.4 | 28.6 | 7.4 | 0 | 0 |
| Condition 12 | 90.5 | 3.1 | 17.8 | 29.5 | 8.4 | 0 | 0 |

TABLE 30-continued

| | Selectivity, Cmol % | | | | |
|---|---|---|---|---|---|
| | Propylene | $C_4$ Olefins | $C_5$ Olefins | $CO_2$ | Oxygenates | $C_3$ fraction in $C_1$-$C_5$ hydrocarbons Cmol % |
| Condition 11 | 0 | 0 | 0 | 41.8 | 0 | 48.3 |
| Condition 12 | 0 | 0 | 0 | 41.0 | 0.13 | 48.6 |

The productivity and selectivity of $C_2$ to $C_5$ paraffins achieved is shown in Table 31 below:

TABLE 31

| | Productivity, g/kg_cat/h | |
|---|---|---|
| | $C_2$-$C_5$ paraffins | Propane |
| Condition 11 | 158.6 | 82.2 |
| Condition 12 | 157.3 | 82.7 |

The $C_3/C_2$ carbon molar ratio of each of the above Examples and Comparative Examples are provided in Table 32 below:

TABLE 32

| | | $C_3/C_2$ carbon molar ratio | Sel. C2 – C3 = (Cmol %) | Conversion (%) |
|---|---|---|---|---|
| Example 1 | Condition 1 | 9 | 0.8 | 33.8 |
| | Condition 2 | 8.9 | 0.9 | 36.7 |
| Example 2 | Condition 1 | 9.4 | 0.8 | 29.9 |
| | Condition 2 | 8.2 | 1.2 | 32.5 |
| Example 3 | Condition 1 | 6.1 | 6.6 | 67.7 |
| | Condition 2 | 7.9 | 0.9 | 75.3 |
| | Condition 3 | 4.8 | 10.1 | 55.5 |
| | Condition 4 | 7.8 | 1.6 | 50.7 |
| Example 4 | Condition 5 | 4.8 | 3.5 | 15.8 |
| | Condition 6 | 4.8 | 1.6 | 34.9 |
| Example 5 | Condition 7 | 9.9 | 1.5 | 37.3 |
| | Condition 8 | 10 | 1.3 | 41.4 |
| Example 6 | Condition 9 | 11.5 | 0.9 | 74.5 |
| Example 7 | Condition 9 | 6.2 | 11.7 | 76.5 |
| Example 8 | Condition 9 | 13.2 | 1 | 74.2 |
| Example 9 | Condition 9 | 9 | 7.1 | 80.9 |
| Example 10 | Condition 10 | 13.6 | 0.8 | 62.7 |
| Example 11 | Condition 11 | 13.1 | 0.6 | 35.6 |
| | Condition 12 | 17 | 0.5 | 63.8 |
| Example 12 | Condition 11 | 10.6 | 0.8 | 38.1 |
| Comparative Example 1 | Condition 9 | 4.8 | 29.9 | 78.4 |
| Comparative Example 2 | Condition 11 | 2.2 | 5 | 23.8 |
| | Condition 12 | 1.9 | 4.5 | 23 |
| Comparative Example 3 | Condition 11 | 1.55 | 0 | 82.0 |
| | Condition 12 | 1.66 | 0 | 90.5 |

Example 1-3 and 5-10 demonstrate that hybrid catalysts comprising a supported metal oxide catalyst component ($Zn/TiO_2$, $In/ZrO_2$, $Ga/ZrO_2$, In—$La/ZrO_2$ or Ga—$La/ZrO_2$) and SSZ-13 as the microporous catalyst component are capable of converting syngas to a mixture of short chain paraffins with selectivity to propane >30 C mol % and $C_3$ fraction in hydrocarbons exceeding 70% at syngas conversion exceeding 25%.

In Example 4, syngas conversion is lower than in Examples 1-3 and 5-10 due to high space velocity chosen for the test. Still selectivity to propane exceeds 30 C mol % and C3 fraction in hydrocarbons is exceeding 60%.

Comparative Example 1 demonstrates that the hybrid catalyst containing the same oxide as in Example 6 and SAPO-34 converts syngas to short chain olefins.

Examples 11-12 demonstrate that hybrid catalysts comprising metal oxide catalyst components and SSZ-13 can operate at temperatures as low as 350-360° C. without methanol/DME break-through (zero selectivity to oxygenates) converting syngas to short chain paraffins with high fraction of $C_3$ exceeding 70%.

Comparative Example 2 shows that the hybrid catalyst comprising same oxide as in Example 11 but with SAPO-34 instead of SSZ-13 converts syngas predominantly to a mixture of oxygenates.

Comparative Example 3 shows that the hybrid catalyst comprising a Cu-based metal oxide component having a high hydrogenation activity towards (olefins) with SSZ-13 as microporous catalyst component converts syngas to a mixture of paraffins with $C_3/C_2$ carbon molar ratio of 1.55-1.67 and $C_3$ fraction not exceeding 50%.

Test Methodology

Catalyst Testing

Catalyst test were performed in a tubular stainless steel (inner diameter of 3 mm) or quartz (inner diameter of 2 mm) fixed-bed microreactor (placed in the stainless steel dome for pressurization). The bottom of the stainless steel reactor was equipped with a metal frit to hold the catalyst bed. The bottom of the quartz reactor was filled with quartz chips with a wool on top to hold the catalyst bed. A hybrid catalyst is loaded to a reactor and the following procedure was used for measuring catalytic activity in conversion of syngas. No activation step was required prior to catalyst testing unless specified otherwise in the description of examples and comparative examples above.

Syngas feed flow [$cm^3$/min STP] per reactor can be calculated using the formula:

$$F = \frac{GHSV \times V_{cat}}{60}$$

Where, GHSV is gas hourly space velocity [$h^{-1}$], $V_{cat}$ is a volume of hybrid catalyst (mL).

Reaction steps used in the examples and comparative examples are as follows:
1) $N_2$ flow, ambient pressure, temperature 25° C., heating to temperature set point from 25° C. at a heating rate of 5° C./min;
2) $N_2$ flow, ambient pressure is changed to pressure set point;
3) $N_2$ is replaced with syngas;
4) Syngas flushing for 1 hour at gas hourly space velocity specified in the Examples and Comparative examples;
5) GC analysis start up (defined as time on stream "zero");
6) Duration of the run is 70-200 h time on stream; and 7) Syngas replaced with $N_2$, cooling down to room temperature, end of the run Products were analyzed by means of the gas chromatography. Online analysis of components ($N_2$, $H_2$, He, CO, $CO_2$, paraffins (also referred to as alkanes) $C_1$-$C_5$, olefins $C_2$-$C_5$) was performed periodically to monitor the reaction progress. The carbon balance in all experiments was 100±5%.

Carbon Monoxide Conversion

Carbon monoxide conversion ($X_{CO}$ [Cmol %]) is defined herein as a percent of carbon in all hydrocarbons produced in the reaction zone to the total amount of carbon released from the reaction zone. The carbon monoxide conversion reported is measured as an average of all data points for a time-on-stream window specified in hours. The formula for calculating the carbon monoxide conversion in the examples is as follows in Equation 1:

$$X_{CO} = \frac{c_{prod}}{c_{total}} \times 100 \tag{1}$$

In Equation 1, $X_{CO}$ is the carbon monoxide conversion, $C_{prod}$ is the amount of carbon (mol/h) in hydrocarbons produced in the reaction zone, and $C_{total}$ is the total amount of carbon (mol/h) leaving the reaction zone.

The $c_{prod}$ is defined as follows in Equation 2:

$$c_{prod} = \Sigma n_i * F_i \tag{2}$$

where $n_i$ is number of carbon atoms in the i-product and $F_i$ is molar flow of i-product exiting the reaction zone (including $CO_2$).

The $c_{total}$ is defined as follows in Equation 3:

$$c_{total} = c_{prod} + F_{CO\_out} \tag{3}$$

where $F_{CO\_out}$ is a molar flow (mol/h) of carbon monoxide leaving the reaction zone.

Selectivity

The selectivity [Cmol %] of i-component for Examples 1-12 and Comparative Examples 1-3 is carbon selectivity defined herein as a percent of carbon in i-product produced in the reaction zone to the total amount of carbon in all products produced in the reaction zone. The selectivity of i-component is measured as an average of all data points for a time-on-stream period specified in the tables. The formula for calculating selectivity is as follows in Equation 4:

$$S_i = \frac{n_i * F_i}{c_{prod}} \times 100 \tag{4}$$

In Equation 4, $S_i$ is the selectivity of i-product, $n_i$ is the amount of carbon atoms in the i-product and $F_i$ is the molar flow (mol/h) of i-product exiting the reaction zone.

$C_3$ Fraction $C_3$ fraction in $C_1$-$C_5$ hydrocarbons is defined as total amount of carbon in $C_3$ products leaving the reaction zone divided by the total amount of carbon in all hydrocarbons (including methane) leaving reaction zone per Equation (5):

$$C3 \text{ fraction in } C1 - C5 \text{ hydrocarbons} = \frac{3 * (F_{propane} + F_{propylene})}{\sum_{i=1}^{5}(n_i * F_i)} \times 100 \tag{5}$$

Where $F_{propane}$ and $F_{propylene}$ are the molar flows [mol/h] of propane and propylene, respectively, leaving the reaction zone; ni—number of carbon atoms in hydrocarbon leaving the reaction zone and Fi—molar flow of hydrocarbon leaving the reaction zone [mol/h].

$C_3/C_2$ carbon molar ratio is defined as ratio of carbon in $C_3$ hydrocarbon products to $C_2$ hydrocarbon products leaving the reaction zone per Equation (6):

$$\frac{C3}{C2} \text{ ratio} = \frac{3 * (F_{propane} + F_{propylene})}{2 * (F_{ethylene} + F_{ethane})} \times 100 \tag{6}$$

Where $F_{propane}$ and $F_{propylene}$ are the molar flows [mol/h] of propane and propylene, respectively, and $F_{ethylene}$ and $F_{ethane}$ are the molar flows [mol/h] of ethylene and ethane, respectively, leaving the reaction zone.

Productivity

The productivity of the hybrid catalyst [g/kg_cat/h] Examples 1-12 and Comparative Examples 1-3 is the amount of $C_2$ to $C_5$ paraffins or $C_2$ to $C_5$ olefins produced compared to the amount of catalyst (mass) used to form the $C_2$ to $C_5$ paraffins or $C_2$ to $C_5$ olefins per unit of time. The productivity may be measured at a given time using the following Equation 7:

$$P_{C2-C5 \, paraffins \, or \, C2-C5 \, olefins} = \frac{\Sigma F_i * M_i}{m_{cat}} \tag{7}$$

In Equation 6, P is the productivity (g/kg_cat/h), $F_i$—is the molar flow of i-component (mol/h) exiting the reaction zone, $M_i$—molar mass of i-component (g/mol) and $m_{cat}$ is total hybrid catalyst mass (kg). Productivity values reported for a specified time-on-stream interval were calculated as average of all data points measured within the specified time-on-stream interval.

Carbon Balance

Carbon balance (CB [Cmol %] is the ratio between total amount of carbon entering the reaction zone in the form of carbon monoxide (mol/h) and leaving the reaction zone in the form of carbon monoxide and carbon-containing products. The formula for calculating the carbon balance is as follows in Equation 8:

$$CB = \frac{c_{total}}{F_{CO\_in}} \times 100 \tag{8}$$

Where $c_{total}$ is total carbon flow [mol/h] leaving the reaction zone and calculated per Equation 3 and $F_{CO\_in}$ in molar flow of CO entering the reaction zone [mol/h].

In Examples 1-12 and Comparative Examples 1-3 the CB was 100±5%.

It will be apparent to those skilled in the art that various modifications and variations can be made to the embodiments described herein without departing from the spirit and scope of the claimed subject matter. Thus, it is intended that the specification cover the modifications and variations of the various embodiments described herein provided such modification and variations come within the scope of the appended claims and their equivalents.

Ammonia TPD Plot for SAPO-34 and SSZ-13

For the determination of the acid sites zeolite or SAPO-34 samples were stored in controlled humidity environment for 24 h (53% relative humidity). $NH_3$— TPD was used for determination of Brönsted acid sites concentration and carried out on a Micromeritics AutoChem II 2920, coupled with a Pfeiffer GSD320 Mass Spectrometer (MS). After cleaning of the sample, typically 100 mg, in Helium for one hour at 500° C. (ramp rate 5° C./min) the sample was cooled down in Helium to 110° C. Afterwards the sample was exposed for 60 minutes to a 10% $NH_3$ in helium gas feed with a flow of 25 ml/min. At the same temperature, the sample was then flushed with helium for 90 minutes to remove excessive $NH_3$ from the sample. When a stable baseline was retrieved, the actual $NH_3$— TPD was performed heating up the sample at 5° C./min to a maximum of 800° C. in Helium. This step was recorded via the build-in TCD (Thermal Conductivity detector) and the MS.

For quantification of the Brönsted acid site concentration a temperature interval of 250-550° C. on the ammonia TPD curve was used. The results are shown in Table 33 below, and graphically in FIG. 1.

TABLE 33

| Material | Brönsted acid site concentration (mmol/g) | Brönsted acid site strength ($T_{max}$) (° C.) |
|---|---|---|
| SAPO-34 | 0.85 | 345 |
| SSZ-13 $SiO_2/Al_2O_3$ = 25 | 0.43 | 417 |
| SSZ-13 $SiO_2/Al_2O_3$ = 30 | 0.49 | 420 |

The invention claimed is:

1. A method for preparing $C_2$ to $C_5$ paraffins comprising:
   introducing a feed stream comprising hydrogen gas and a carbon-containing gas selected from the group consisting of carbon monoxide, carbon dioxide, and mixtures thereof into a reaction zone of a reactor; and
   converting the feed stream into a product stream comprising $C_2$ to $C_5$ paraffins in the reaction zone in the presence of a hybrid catalyst, the hybrid catalyst comprising:
   a microporous catalyst component; and
   a metal oxide catalyst component comprising a metal component present on a metal oxide support material, wherein the metal oxide support material comprises at least one oxide of a metal selected from Group 4 of the IUPAC periodic table of elements,
   wherein the product stream has a $C_3/C_2$ carbon molar ratio greater than or equal to 4.0.

2. The method of claim 1, wherein the microporous catalyst component is a molecular sieve having 8-MR pore openings.

3. The method of claim 1, wherein the microporous catalyst component is silico-aluminate having a Chabazite structure.

4. The method of claim 1, wherein the microporous catalyst component is SSZ-13.

5. The method of claim 1, wherein a Brönsted acid site concentration of the microporous catalyst component is greater than or equal to 0.25 mmol/g, and a Brönsted acid site strength from 380° C. to 500° C. measured as $NH_3$-desorption at rate of 5° C./min.

6. The method of claim 1, wherein a Brönsted acid site concentration of the microporous catalyst component is greater than or equal to 0.35 mmol/g, and a Brönsted acid site strength from 400° C. to 500° C. measured as $NH_3$-desorption at rate of 5° C./min.

7. The method of claim 1, where in the metal component of the metal oxide catalyst component is selected from the group consisting of zinc, gallium, indium, lanthanum, chromium and mixtures thereof.

8. The method of claim 1, wherein the metal oxide support material comprises titania or zirconia.

9. The method of claim 1, wherein the metal component comprises from 0.1 wt % to 10.0 wt % of the metal oxide catalyst component.

10. The method of claim 1, wherein an amount of $C_3$ paraffins in the product stream as a carbon mole percent of a total of $C_1$ to $C_5$ hydrocarbons in a product stream is greater than or equal to 50.0 mol %.

11. The method of claim 1, wherein an amount of $C_3$ paraffins in the product stream as a carbon mole percent of a total of $C_1$ to $C_5$ hydrocarbons in a product stream is greater than or equal to 70.0 mol %.

12. The method of claim 1, wherein the product stream has a $C_3/C_2$ carbon molar ratio greater than or equal to 5.0.

13. The method of claim 1, wherein the product stream has a $C_3/C_2$ carbon molar ratio greater than or equal to 8.0.

* * * * *